(12) United States Patent
Sakano et al.

(10) Patent No.: US 7,785,310 B2
(45) Date of Patent: Aug. 31, 2010

(54) DISPOSABLE DIAPER

(75) Inventors: Katsushi Sakano, Kasugai (JP);
Katsuhiko Sugiyama, Tokyo (JP);
Izumi Tashiro, Tokyo (JP); Tomotsugu Miyoshi, Tokyo (JP)

(73) Assignees: Oji Nepia Co., Ltd., Chuo-ku (JP); Oji Paper Co., Ltd., Chuo-ku (JP)

( * ) Notice: Subject to any disclaimer, the term of this patent is extended or adjusted under 35 U.S.C. 154(b) by 0 days.

(21) Appl. No.: 11/545,724

(22) Filed: Oct. 10, 2006

(65) Prior Publication Data
US 2007/0088304 A1    Apr. 19, 2007

(30) Foreign Application Priority Data

Oct. 14, 2005   (JP)   ............... 2005-300392
Jan. 31, 2006   (JP)   ............... 2006-023347

(51) Int. Cl.
*A61F 13/15*    (2006.01)
(52) U.S. Cl. ............ 604/385.101; 604/385.27; 604/385.28; 604/385.08; 604/385.01; 604/385.19; 604/385.14; 604/378
(58) Field of Classification Search ............ 604/385.24, 604/385.26, 385.28, 385.29, 385.3, 378, 604/381, 382, 385.01, 385.101, 385.22, 385.19, 604/385.14, 385.04, 385.08, 385.27
See application file for complete search history.

(56) References Cited

U.S. PATENT DOCUMENTS

| | | | |
|---|---|---|---|
| 4,662,877 A | 5/1987 | Williams | |
| 6,409,711 B1* | 6/2002 | Jonbrink | 604/385.01 |
| 6,632,212 B1* | 10/2003 | Morman et al. | 604/385.22 |
| 2004/0039363 A1 | 2/2004 | Sugiyama et al. | |
| 2004/0092900 A1* | 5/2004 | Hoffman et al. | 604/380 |

FOREIGN PATENT DOCUMENTS

| | | |
|---|---|---|
| GB | 2 268 073 | 1/1994 |
| JP | 2572744 | 10/1996 |
| JP | 2559050 | 9/1997 |
| JP | 2002-011044 | 1/2002 |
| JP | 2002-204811 | 7/2002 |

* cited by examiner

*Primary Examiner*—Jacqueline F. Stephens
(74) *Attorney, Agent, or Firm*—Burr & Brown (57) ABSTRACT

A disposable diaper is provided, including an absorber, a top sheet arranged to cover the top surface of the absorber, a back sheet arranged to cover the bottom surface of the absorber, and a skin-contact sheet arranged over the top sheet. The top sheet is at least partially composed of a liquid-permeable material, the back sheet is composed of a liquid-impermeable material, and the skin-contact sheet is at least partially composed of a breathable waterproof sheet and is provided with a feces-passing opening capable of allowing feces to pass therethrough.

7 Claims, 8 Drawing Sheets

DISPOSABLE DIAPER

BACKGROUND OF THE INVENTION

1. Field of the Invention

The present invention relates to disposable diapers including absorbers, top sheets, back sheets, and skin-contact sheets. The skin-contact sheets are arranged over the top sheets and are provided with openings to allow passage of feces.

2. Description of the Related Art

Recently, disposable diapers including an absorber, a top sheet, and a back sheet have been widely used as diapers for infants and elderly or disabled persons. The top sheet is arranged so as to cover the top surface of the absorber and is at least partially composed of a liquid-permeable material. The back sheet is arranged so as to cover the bottom surface of the absorber and is composed of a liquid-impermeable material. This disposable diaper is worn by a wearer so that the surface of the top sheet is in contact with the skin of the wearer, and thereby urine excreted by the wearer penetrates the top sheet and is absorbed and held by the absorber. The back sheet is superior in the prevention of leakage of excrement, and thereby the leakage of excrement to the outside of the diaper is prevented (see, for example, FIG. 3 in Japanese Patent No. 2572744: Patent Document 1).

However, in a diaper having the above-described structure, urine can penetrate the top sheet, but most feces cannot penetrate the top sheet. Therefore, the feces remain on the top sheet. The remaining feces on the top sheet adhere to the crotch area and buttock area of a wearer, and, consequently, troublesome wiping-off work is required to clean the wearer. This causes an increase in the burden on nursing infants or care-givers, and also causes skin irritation to a wearer. These troubles are further significant when a wearer excretes soft feces.

Accordingly, disposable diapers including an additional sheet (in this specification, termed a "skin-contact sheet") disposed over the top sheet have been disclosed (see, for example, paragraph 0010 and FIG. 2 in Japanese Utility Model Registration No. 2559050: Patent Document 2, and paragraph 0020 and FIG. 1 in Japanese Unexamined Patent Application Publication No. 2002-11044: Patent Document 3). In these disposable diapers, the skin-contact sheet is provided with an opening (feces-passing opening) allowing passage of feces, and feces excreted by a wearer pass through the feces-passing opening and reach the top sheet.

In the disposable diapers disclosed in Patent Documents 2 and 3, the skin-contact sheet is brought into contact with the skin of a wearer and the top sheet arranged under the skin-contact sheet is negligibly brought into direct contact with the skin of the wearer. Thus, the top sheet is isolated from the skin of a wearer by the skin-contact sheet interposed between the top sheet and the skin of the wearer. That is, the skin-contact sheet serves as a shielding layer. Therefore, it is expected that, even if feces remain on the top sheet, the opportunity that the feces are brought into direct contact with the skin of a wearer is significantly decreased.

However, even if a disposable diaper has a skin-contact sheet described above, urine or soft feces that have reached the top sheet through the skin-contact sheet sometimes exude from the skin-contact sheet and adhere to the skin of a wearer. These occurrences, so-called "urine backflow and feces backflow", are problematic. In other words, the disposable diaper provided with the skin-contact sheet is not sufficiently satisfactory from the viewpoint of the prevention of urine backflow and feces backflow and therefore still has problems to be solved.

Thus, at present, disposable diapers which can allow the skin of a wearer to be negligibly brought into direct contact with excreted feces and can efficiently prevent urine backflow and feces backflow have not been disclosed yet, and such disposable diapers are desired to be developed. The present invention has been accomplished for solving the problems of the known technologies and provides disposable diapers which can allow the skin of a wearer to be negligibly brought into direct contact with excreted feces and can efficiently prevent urine backflow and feces backflow.

SUMMARY OF THE INVENTION

The present inventors have conducted intensive studies in an attempt to solve the above-mentioned problems in known technologies, and have found that some skin-contact sheets provided to known disposable diapers are composed of liquid-permeable sheets (hydrophilic sheets) and, in such cases, urine and feces penetrate the skin-contact sheet and exude from the skin-contact sheet to the surface to readily cause urine backflow or feces backflow. In addition, the present inventors have arrived at the conclusion that the above-mentioned problems can be solved by constituting at least a part of the skin-contact sheet with a breathable waterproof sheet. Thus, the present invention has been accomplished. Specifically, in accordance with the present invention, the following disposable diapers are provided.

According to a first aspect of the present invention, a disposable diaper is provided, including an absorber, a top sheet arranged so as to cover the top surface of the absorber, a back sheet arranged so as to cover the bottom surface of the absorber, and a skin-contact sheet arranged over the top sheet. The top sheet is at least partially composed of a liquid-permeable material. The back sheet is composed of a liquid-impermeable material. The skin-contact sheet is at least partially composed of a breathable waterproof sheet and is provided with an opening (feces-passing opening) allowing passage of feces.

According to a second aspect of the present invention, the disposable diaper according to the first aspect further includes a liquid-permeation resistive layer disposed on the upper side and/or lower side of the breathable waterproof sheet.

According to a third aspect of the present invention, in the disposable diaper according to the second aspect, the liquid-permeation resistive layer includes a hot-melt adhesive layer composed of a coated hot-melt adhesive in the range of 15 to 40 $g/m^2$, and the hot-melt adhesive layer is disposed on the lower side of the breathable waterproof sheet.

According to a fourth aspect of the present invention, in the disposable diaper according to the second or third aspects, the liquid-permeation resistive layer includes a water-repellent agent layer composed of a coated water-repellent agent containing wax, and the water-repellent agent layer is disposed on the upper side of the breathable waterproof sheet.

According to a fifth aspect of the present invention, in the disposable diaper according to any one of the first to fourth aspects, the skin-contact sheet is partially provided with a liquid-permeable portion.

According to a sixth aspect of the present invention, in the disposable diaper according to the fifth aspect, the skin-contact sheet is partially composed of a liquid-permeable sheet, and the liquid-permeable sheet serves as the liquid-permeable portion.

According to a seventh aspect of the present invention, in the disposable diaper according to the sixth aspect, the skin-contact sheet is composed of a laminate of the breathable waterproof sheet and the liquid-permeable sheet, and the laminate has a structure such that the breathable waterproof sheet is arranged at the central region of the liquid-permeable sheet and the liquid-permeable sheet protrudes from both sides of the breathable waterproof sheet.

According to an eighth aspect of the present invention, in the disposable diaper according to the seventh aspect, the skin-contact sheet is composed of a laminate having a structure such that the breathable waterproof sheet is laminated on the top surface of the liquid-permeable sheet.

According to a ninth aspect of the present invention, the disposable diaper according to any one of the first to eighth aspects further includes at least a pair of standing gathers disposed on the respective side edges of the skin-contact sheet so as to be able to stand for serving as leakage-preventing walls.

The disposable diapers according to the present invention can allow the skin of a wearer to be negligibly brought into direct contact with excreted feces and can efficiently prevent urine backflow and feces backflow.

DESCRIPTION OF THE PREFERRED EMBODIMENTS

Best mode for carrying out the disposable diapers according to the present invention will now be specifically described with reference to a pants-type diaper composed of two pieces. However, the present invention is not limited to the following embodiments, but broadly includes disposable diapers satisfying features of the present invention. In addition, leg elastic members are eliminated in FIGS. 3 to 8 as a matter of convenience for drawing.

In this specification, the term "pants-type diaper" refers to a diaper previously formed into a form of pants. Like the disposable diaper 1 shown in FIGS. 1 and 2, margins at the sides of a front part 2 are bonded to the corresponding margins of a back part 6 (the margins 2a and 2b are bonded to the margins 6a and 6b, respectively), and thereby joints 8, an opening around waist 10, and a pair of openings around legs 12a and 12b are formed. The term "two-piece type" refers to a diaper composed of an absorbent body 14 being capable of absorbing and holding excrement of a wearer (absorbing and holding functions) and a wearing member 16 for putting the diaper to the body of a wearer (wearing function), and the absorbent body 14 is arranged on the inside of the wearing member 16. As shown in FIG. 3, the absorbent body 14 is composed of an absorber 22, a top sheet 18, and a back sheet 20.

In this specification, the term "front part" refers to a part covering an abdominal side (the front of body) of a wearer of the diaper, the term "crotch portion" refers to a part covering the crotch area of a wearer of the diaper, and the term "back part" refers to a part covering a back side (the back of body) of a wearer of the diaper.

Figure 1:
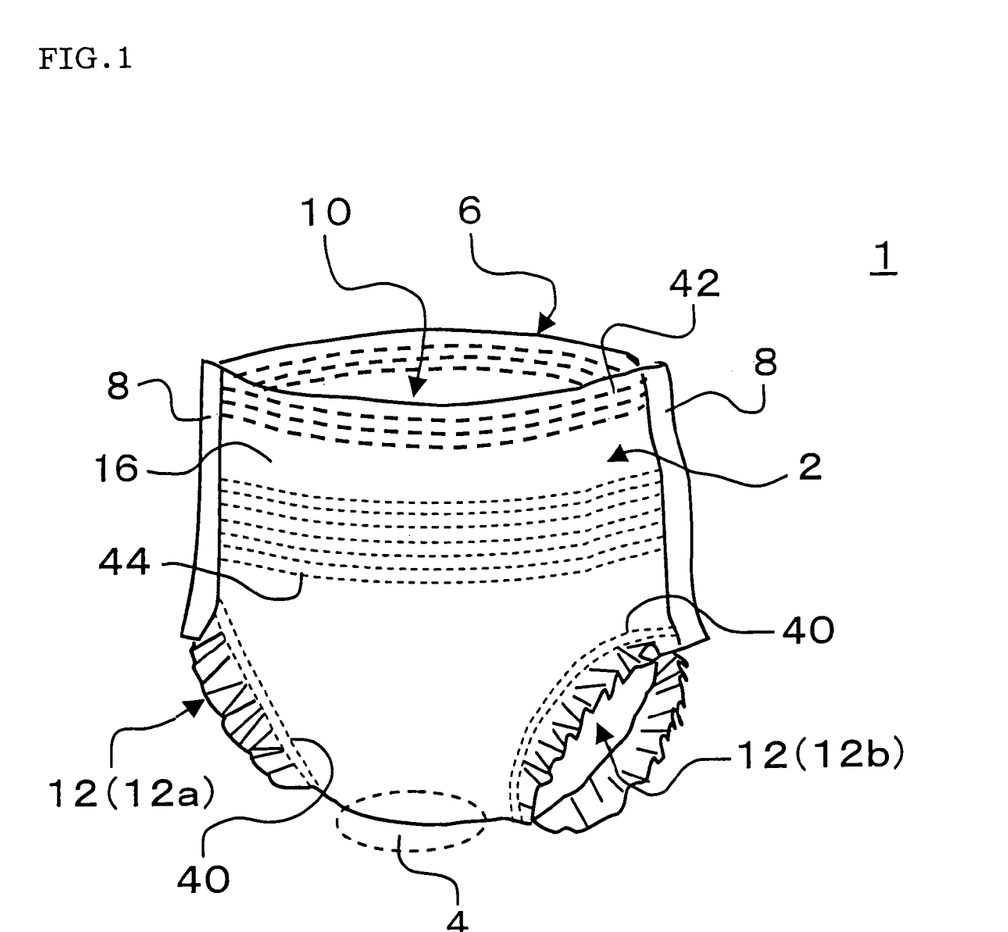
FIG. 1 is a schematic perspective view of a disposable diaper according to an embodiment of the present invention when viewed from the front.
Figure 2:
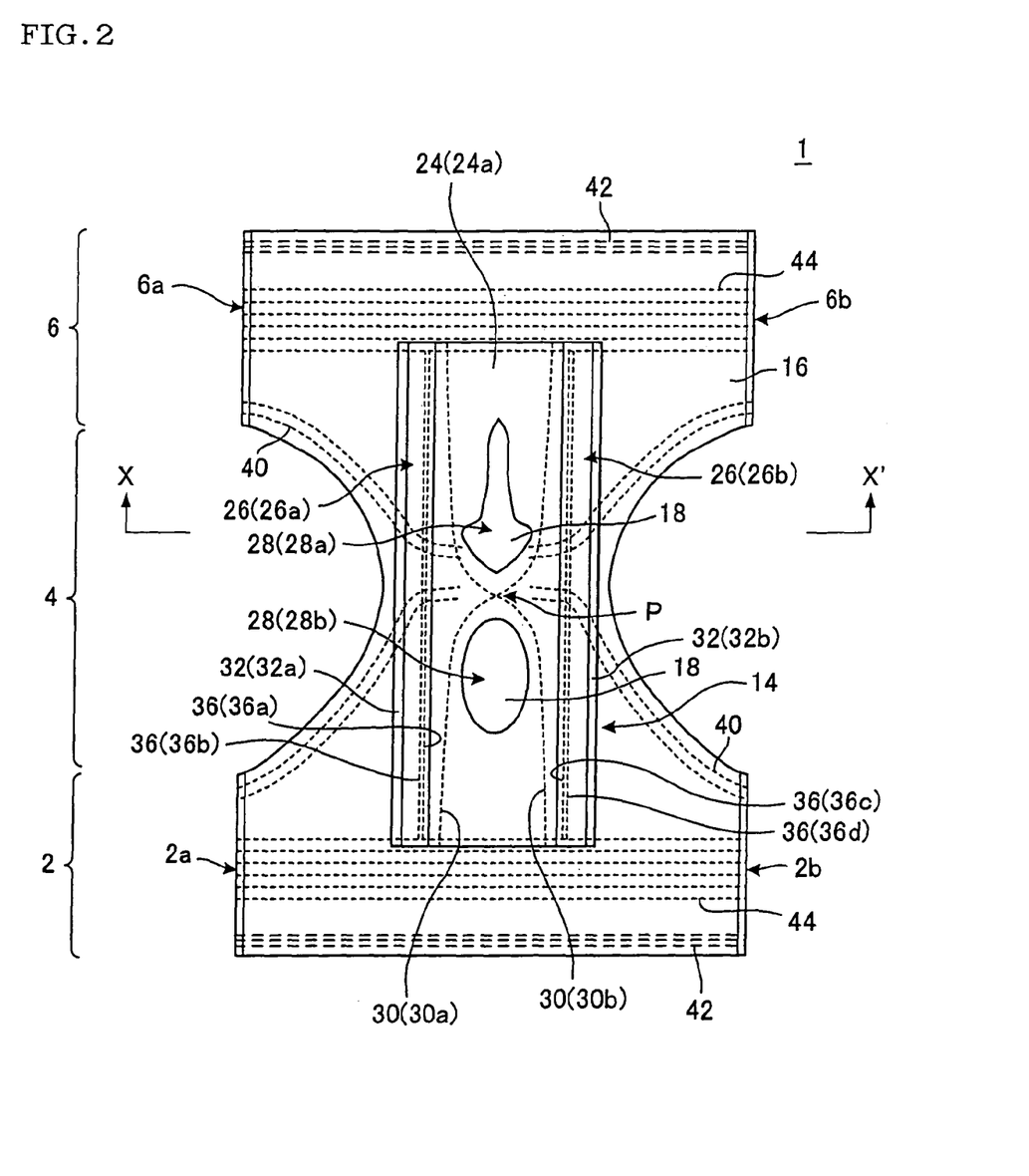
FIG. 2 is a developed plan view of the disposable diaper shown in FIG. 1 according to the embodiment of the present invention when viewed from the absorbent body side of the diaper.
Figure 3:
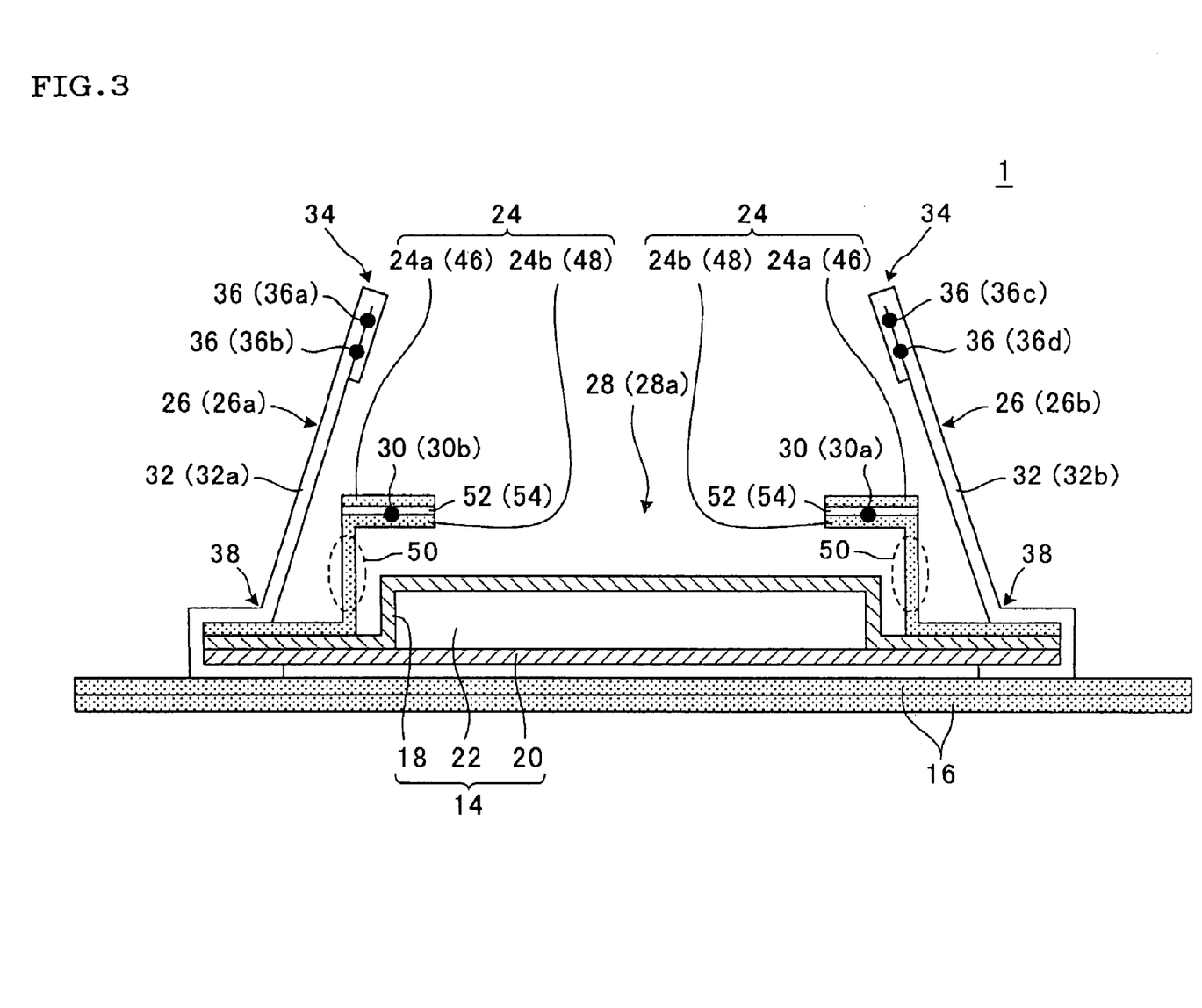
FIG. 3 is a schematic cross-sectional view taken along the line X-X' of FIG. 2 showing the disposable diaper according to the embodiment of the present invention.

(1) Structure of Disposable Diaper in Accordance with the Present Invention:

A disposable diaper in accordance with the present invention is provided with a top sheet 18, a back sheet 20, and an absorber 22 interposed between at least a part of the top sheet 18 and the back sheet 20, like the disposable diaper 1 shown in FIGS. 1 to 3. The disposable diaper is further provided with a skin-contact sheet 24 arranged over the surface of the top sheet 18. At least a part of the skin-contact sheet 24 is composed of a breathable waterproof sheet 46.

(1-1) Skin-Contact Sheet:

The skin-contact sheet is arranged over the top sheet and serves as a member for isolating the skin of a wearer from the top sheet. The skin-contact sheet is a sheet-like member provided with an opening (feces-passing opening) for allowing passage of feces. By providing the skin-contact sheet to a diaper, the skin of a wearer of the diaper is firstly brought into contact with the skin-contact sheet. Consequently, the top sheet arranged under the skin-contact sheet is negligibly brought into direct contact with the skin of a wearer. That is, the skin of a wearer and the top sheet are isolated from each other. In addition, the skin-contact sheet serving as a shielding layer is interposed between the top sheet and the skin of a wearer. Therefore, it is expected that, even if feces remain on the top sheet, the opportunity that the feces are brought into direct contact with the skin of the wearer is significantly decreased.

Examples of materials constituting the skin-contact sheet include non-woven fabrics, sheets, and films, which are composed of a resin such as polyethylene, polypropylene, or polyester. In particular, non-woven fabrics are preferable because of their pleasantness of touch. These materials may be liquid-permeable, liquid-impermeable, or water repellent.

However, in the disposable diaper in accordance with the present invention, the skin-contact sheet must be at least partially composed of a breathable waterproof sheet. The portion composed of the breathable waterproof sheet can obviously maintain the comfortableness (dry-touch property) even when the diaper is worn for a long period of time, and also can decrease the liquid permeability. Therefore, urine or soft feces that have reached the top sheet through the skin-contact sheet can be efficiently prevented from exuding from the skin-contact sheet and from adhering to the skin of a wearer (prevent from so-called "urine backflow and feces backflow"). The disposable diaper 1 shown in FIGS. 1 to 3 is an example that an upper sheet 24a, which is a part of the skin-contact sheet 24, is composed of a breathable waterproof sheet 46. Since the skin-contact sheet 24 must be "at least partially" composed of a breathable waterproof sheet 46, the entire skin-contact sheet 24 may be composed of a breathable waterproof sheet 46.

Materials constituting the breathable waterproof sheet include non-woven fabrics such as spunbond and card emboss. SMS (spunbond-meltblown-spunbond composite) and SMMS (spunbond-meltblown-meltblown-spunbond composite) are preferable non-woven fabrics because of their high water-pressure resistance.

When a part of the skin-contact sheet is formed of a breathable waterproof sheet, it is preferable that a liquid-permeation resistive layer is disposed on the upper side and/or lower side of the breathable waterproof sheet. The breathable waterproof sheet has water repellency, but is not completely liquid-impermeable. Therefore, when the buttock area of a wearer is put on the skin-contact sheet and the body weight of the wearer is applied to the skin-contact sheet, urine or soft feces once passed through the skin-contact sheet may exude from the surface of the skin-contact sheet. Therefore, the exudation of urine and soft feces (namely, urine backflow and feces backflow) is sufficiently prevented by constituting a part of the skin-contact sheet with a breathable waterproof sheet and simultaneously providing a liquid-permeation resistive layer on the upper side and/or lower side of the breathable waterproof sheet.

The formation of such a liquid-permeation resistive layer is particularly effective when the skin-contact sheet 24 is composed of a laminate of a liquid-permeable sheet 48 and a breathable waterproof sheet 46 as in the disposable diaper 1 shown in FIG. 3. The liquid permeability of the liquid-permeable sheet is usually improved by applying a hydrophilicity-imparting agent (for example, surface-active agent) to a non-woven fabric. This hydrophilicity-imparting agent is sometimes dispersed with urine penetrated in the liquid-permeable sheet and thereby is transferred to the breathable waterproof sheet. Consequently, the water repellency of the breathable waterproof sheet is decreased with the passage of time, and urine backflow and feces backflow may be induced. In the present invention, the urine backflow and feces backflow due to the transferred hydrophilicity-imparting agent can be effectively prevented by constituting a part of the skin-contact sheet with a breathable waterproof sheet and additionally providing a liquid-permeation resistive layer on the upper side and/or lower side of the breathable waterproof sheet. That is, stickiness of the skin-contact sheet after excretion can be decreased and comfortable wearing can be achieved.

In this specification, the term "liquid-permeation resistive layer" refers to a layer composed of a material having a property to prevent the permeation of liquid and having a property to further decrease the liquid permeability of the breathable waterproof sheet. The constitution of the liquid-permeation resistive layer is not specifically limited as long as the layer has such properties. For example, the liquid-permeation resistive layer may be prepared by attaching a liquid-impermeable film or sheet of a material which may be used for the back sheet to the breathable waterproof sheet. In the present invention, the liquid-permeation resistive layer is preferably prepared by coating (applying) a material blocking the permeation of liquid on a breathable waterproof sheet.

Figure 4:
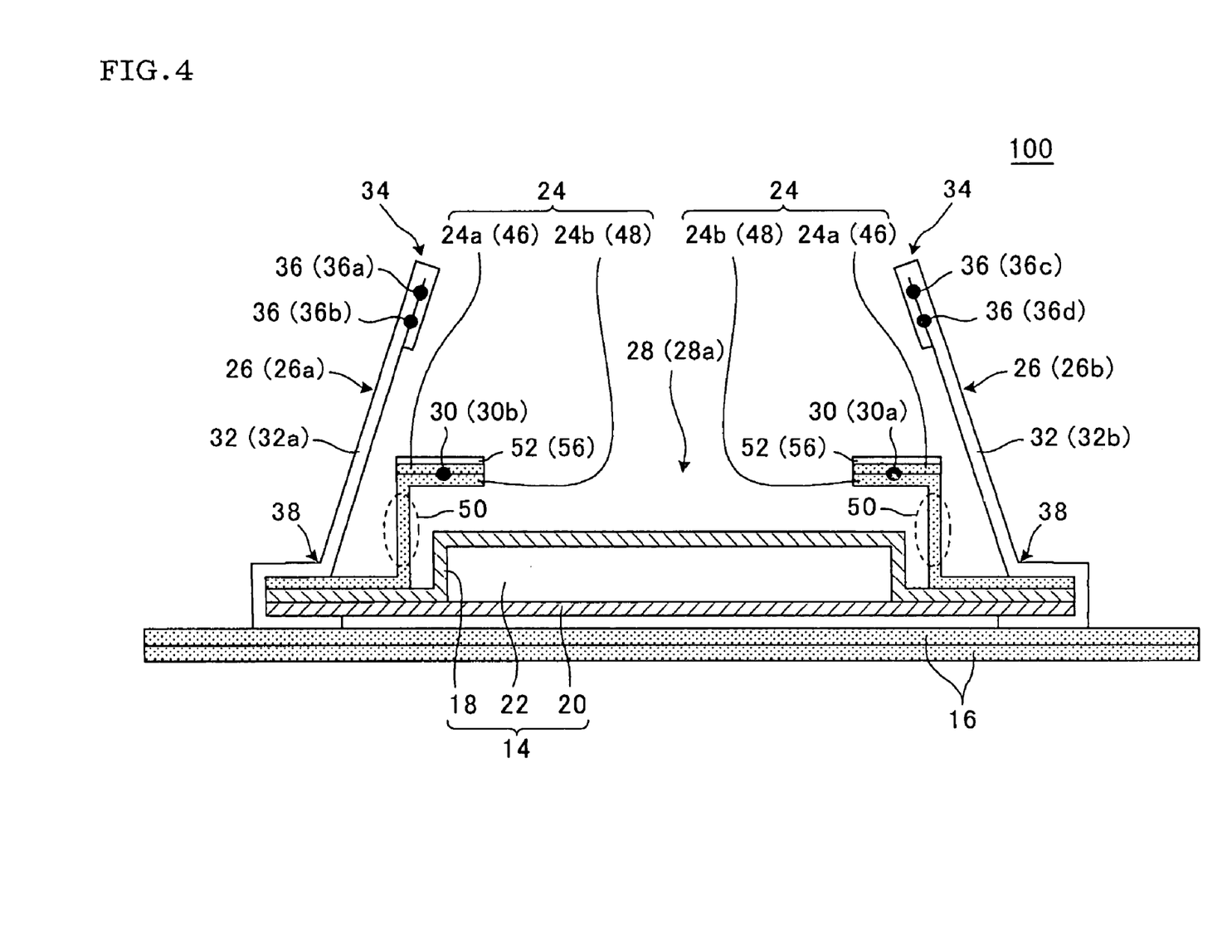
FIG. 4 is a schematic cross-sectional view of a disposable diaper according to another embodiment of the present invention, showing a cross section when the disposable diaper is cut at a crotch portion.
Figure 5:
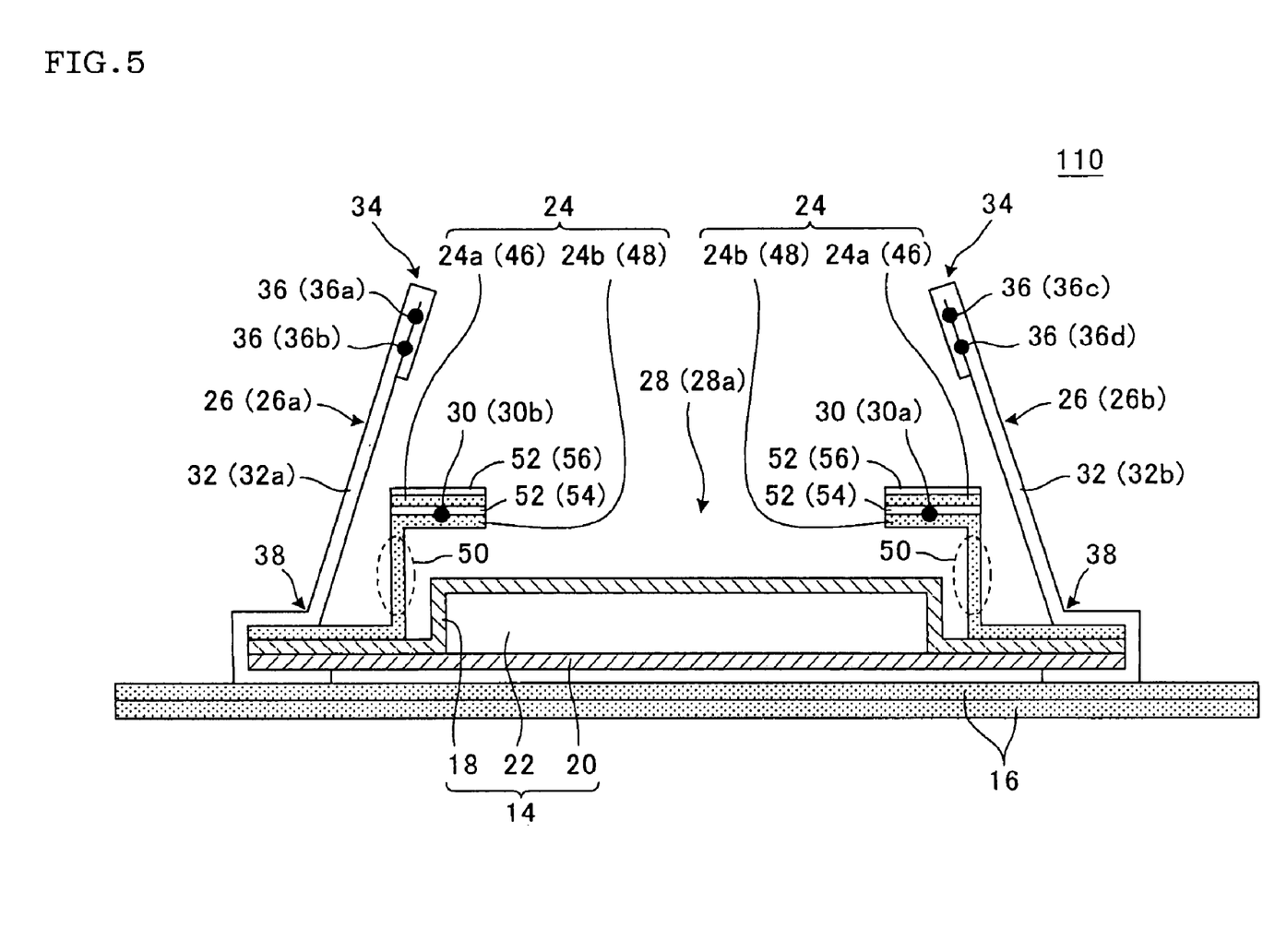
FIG. 5 is a schematic cross-sectional view of a disposable diaper according to another embodiment of the present invention, showing a cross section when the disposable diaper is cut at a crotch portion.
Figure 6:
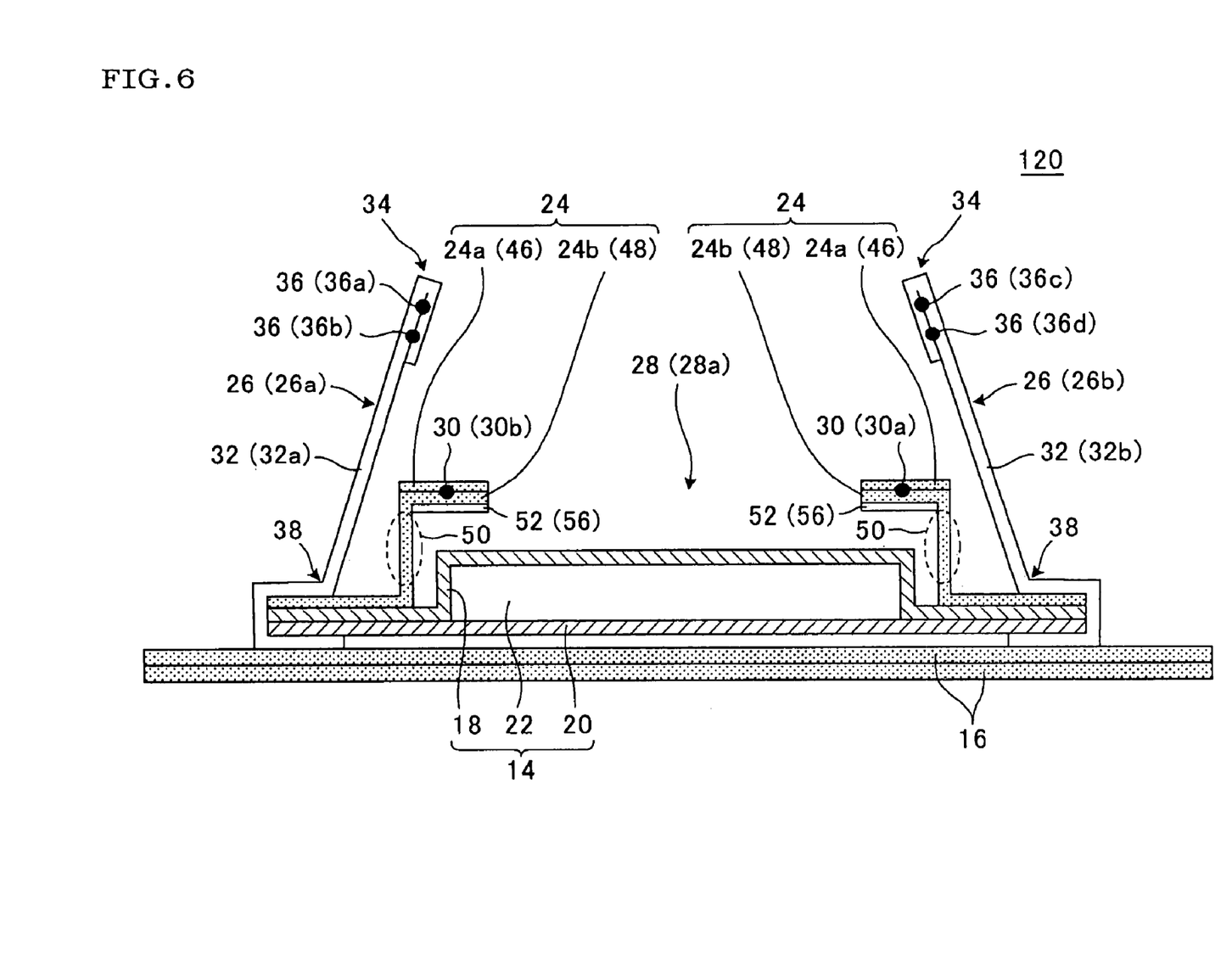
FIG. 6 is a schematic cross-sectional view of a disposable diaper according to another embodiment of the present invention, showing a cross section when the disposable diaper is cut at a crotch portion.

The liquid-permeation resistive layer may be disposed on the upper side, lower side, or both sides of the breathable waterproof sheet. For example, the disposable diaper 1 shown in FIG. 3 is an example that the liquid-permeation resistive layer 52 is disposed on the lower side of the breathable waterproof sheet 46. In addition, the disposable diaper 100 shown in FIG. 4 is an example that the liquid-permeation resistive layer 52 is disposed on the upper side of the breathable waterproof sheet 46, and the disposable diaper 110 shown in FIG. 5 is an example that the liquid-permeation resistive layers 52 are disposed on the upper and lower sides of the liquid-permeation resistive layer 52.

In the present invention, the formation of the liquid-permeation resistive layer does not have any limitation as long as the liquid-permeation resistive layer is disposed on "the upper side" and/or "the lower side" of the breathable waterproof sheet. In other words, the liquid-permeation resistive layer may be partially disposed over the top surface or the bottom surface of the breathable waterproof sheet, or may be disposed so as to protrude through the top surface or the bottom surface of the breathable waterproof sheet.

In addition, in the present invention, the liquid-permeation resistive layer is not required to be disposed directly on the top surface or the bottom surface of the breathable waterproof sheet as long as the liquid-permeation resistive layer is disposed on "the upper side" and/or "the lower side" of the breathable waterproof sheet. In other words, any layers may be interposed between the breathable waterproof sheet and the liquid-permeation resistive layer. For example, in a disposable diaper 120 shown in FIG. 6, the liquid-permeation resistive layer 52 is not directly disposed on the bottom surface of the breathable waterproof sheet 46. The liquid-permeation resistive layer 52 is disposed on the bottom surface of the liquid-permeable sheet 48 which is attached to the bottom surface of the breathable waterproof sheet 46. That is, the liquid-permeable sheet 48 is interposed between the breathable waterproof sheet 46 and the liquid-permeation resistive layer 52.

In the disposable diaper in accordance with the present invention, the liquid-permeation resistive layer is preferably a hot-melt adhesive layer. The hot-melt adhesive layer includes a coated hot-melt adhesive agent. A thermoplastic resin (base polymer) contained in the hot-melt adhesive agent has a property to prevent the permeation of liquid and, therefore, is suitably used as a material for forming a liquid-permeation resistive layer.

In general, a hot-melt adhesive agent is composed of (1) a base polymer such as an ethylene-vinylacetate copolymer (EVA), an ethylene-ethyl acrylate copolymer (EEA), a styrene-butadiene block copolymer (SBS), or a styrene-isoprene block copolymer (SIS), (2) a tackifier such as a rosin derivative or a petroleum resin, (3) a diluent such as oil or wax (paraffin), and (4) other components (antioxidant and the like). In the present invention, hot-melt adhesive agents used in hygienic goods such as disposable diapers and sanitary napkins may be used. Specifically, hot-melt adhesive agents containing a SBS, a SIS, a hydrogenated SBS (SEBS), or a hydrogenated SIS (SEPS) as the base polymer are preferably used.

When the liquid-permeation resistive layer is a hot-melt adhesive layer, the hot-melt adhesive layer is preferably disposed on the lower side of the breathable waterproof sheet. By providing the hot-melt adhesive layer at such a position, the skin of a wearer is prevented from being brought into direct contact with the hot-melt adhesive agent. For example, in the disposable diaper 1 shown in FIG. 3, a hot-melt adhesive layer 54 to be formed into a liquid-permeation resistive layer 52 is disposed on the lower side of a breathable waterproof sheet 46 (specifically, between a breathable waterproof sheet 46 and a liquid-permeable sheet 48 constituting a skin-contact sheet 24).

When the liquid-permeation resistive layer is a hot-melt adhesive layer, a hot-melt adhesive agent is coated in the range of 15 to 40 g/m². The hot-melt adhesive agent may be used for bonding non-woven fabrics in a manufacturing process of disposable diapers, but the amount of the hot-melt adhesive agent used in such a case is about 10 g/m² at most. On the other hand, in the present invention, the amount of the hot-melt adhesive agent is at least 15 g/m² for sufficiently preventing the permeation of liquid. However, the coating amount of higher than 40 g/m² makes the texture of the skin-contact sheet hard. In addition, the hot-melt adhesive agent in such an amount may be squeezed out from the bottom surface of the breathable waterproof sheet and, thereby, may be brought into direct contact with the skin of a wearer.

In the disposable diaper according to the present invention, the liquid-permeation resistive layer may be preferably a water-repellent agent layer. The water-repellent agent layer includes a coated water-repellent agent containing wax. The wax contained in the water-repellent agent has a property to prevent the permeation of liquid and, therefore, is suitably used as a material for forming a liquid-permeation resistive layer.

In this specification, the term "water-repellent agent" refers a composite which has a property to prevent the permeation of liquid by its high water-repellency and is solid at an ordinary temperature (25° C.). Specifically, a composite containing wax as an essential component and optically containing additives, depending on the purpose, such as a ductile agent, oil, a skin-care component (moisturizing agent, antiphlogistic agent, and the like), a thickener, an antiseptic, and a surface-active agent, can be suitably used. Since the skin-contact sheet is a member being in contact with the skin of a wearer at all times, skin irritation may occur by abrading the skin of the wearer with the skin-contact sheet. Therefore, the friction between the skin of a wearer and the layer can be decreased by coating the sheet with the above-mentioned composite. In addition, the skin of a wearer is actively cared by the skin-care components which are contained in the composite.

The "wax" is a component for adding a high water-repellent property to a water-repellent agent and serving as a base material for blending additives. Examples of the wax include known wax, i.e., beeswax, carnauba wax, paraffin wax, petrolatum, purified lanolin, and vegetable stearic acid. The "ductile agent" is a component for decreasing the viscosity of the wax and adding ductility (good stretchiness) to the wax. Examples of the ductile agent include stearic acid, ethylene glycol fatty acid ester, glycerin, vegetable glycerin, Catanol, propylene glycol, and monostearic acid polyethylene glycol.

Examples of the "oil" include avocado oil, emu oil, olibanum oil, olive oil, cajeput oil, grape seed oil, vegetable stearic acid, sweet almond oil, squalane, stearyl alcohol, geranium oil, palm oil, horse oil, jojoba oil, and liquid paraffin. These oils are superior in affinity with skins of persons and serve as skin-protective components. Examples of the "skin-care components" include components combating skin disorders, such as allantoin, melaleuca oil, and coix seed extract; components having antiphlogistic and moisturizing activity, such as aloe vera; components having antibacterial activity, such as dwarf bamboo extract; components having activity for curing dermatitis, such as glycyrrhizic acid, β-glycyrrhizic acid, borage oil, vitamin C, and saxifrage carmentosa extract; components having antiinflammatory activity, such as stearyl glycyrrhizinate, shikon extract, German chamomile oil, and mogwort extract; and components having moisturizing activity, such as vegetable squalane, trehalose, urea, pyrrolidone carboxylate, betaine, eucalyptus extract, and rose hip oil.

Examples of the "thickener" include titanium mica, zinc oxide, titanium oxide, silk powder, talc, pearl powder, and methyl polysiloxane. By the addition of these materials, the water-repellent agent is provided with viscosity suitable for coating and, thereby, is improved in the coating property. In addition, the shiny appearance, which is not preferred as disposable diaper appearance, is decreased. Examples of the "antiseptic" include ethylparaben, methylparaben, and phenoxyethanol. Examples of the "surface-active agent" include sodium cocoyl glutamate. By the addition of the surface-active agent, compatibility between the wax and various types of additives can be improved.

The water-repellent agent can be prepared by melting wax as the base material by heating, and mixing an adequate amount of proper additives with the wax in the melted state. The amount of the wax is preferably 10 to 90 mass % with respect to the total mass of the water-repellent agent.

When the liquid-permeation resistive layer is disposed on the upper side of the breathable waterproof sheet, the liquid-permeation resistive layer is preferably a water-repellent agent layer. As described above, the water-repellent agent layer can contain a skin-protecting component, and irritation to skin of a wearer can be decreased compared to a case using a hot-melt adhesive agent. For example, in the disposable diaper 1 shown in FIG. 4, a water-repellent agent layer 56 to be formed to a liquid-permeation resistive layer 52 is disposed on the upper side of a breathable waterproof sheet 46 (specifically, disposed directly on the upper surface of the breathable waterproof sheet 46).

When the liquid-permeation resistive layer is a water-repellent agent layer, a water-repellent agent is coated in the range of 1 to 30 g/m², more preferably, in the range of 3 to 10 g/m². By the coated water-repellent agent in the range of 1 to 30 g/m², stickiness to skin and degradation of feel can be prevented and, simultaneously, liquid-permeation resistance can be sufficiently achieved. On the other hand, when the amount of a water-repellent agent is less than 3 g/m², the liquid-permeation resistance may not be sufficiently achieved. When the amount of the water-repellent agent is higher than 20 g/m², the liquid-permeation resistance may not be sufficiently achieved.

When the liquid-permeation resistive layers are disposed on both the upper and lower sides of the breathable waterproof sheet, for example, as in the disposable diaper 110 shown in FIG. 5, it is preferable that a water-repellent agent layer 56 is disposed on the upper side of the breathable waterproof sheet 46 (specifically, disposed directly on the upper surface of the breathable waterproof sheet 46) and a hot-melt adhesive layer 54 is disposed on the lower side of the breathable waterproof sheet 46 (specifically, disposed between the breathable waterproof sheet 46 and the liquid-permeable sheet 48). With such a configuration, higher liquid-permeation resistance can be achieved compared with that in a case that the liquid-permeation resistive layer 52 is a single layer. In addition, irritation to skin of a wearer is advantageously low.

When a part of the skin-contact sheet is composed of a breathable waterproof sheet, it is preferable that the skin-contact sheet be partially provided with a liquid-permeable portion. In a diaper having a skin-contact sheet, urine may be excreted on the skin-contact sheet. In such a case, the urine remains on the skin-contact sheet and is not absorbed by the absorber if the entire skin-contact layer is composed of a breathable waterproof sheet having a low liquid permeability. Therefore, the urine may adhere to the skin of a wearer or urine leakage from an opening around legs of a diaper (so-called "side leakage") may occur. On the other hand, in the above-mentioned structure, urine passes through the liquid-permeable portion of the skin-contact sheet and is introduced to the inside of the skin-contact sheet. Consequently, troubles such as adhesion of urine to the skin of a wearer or side leakage of urine can be effectively prevented.

A liquid-permeable portion may be formed on a part of the skin-contact sheet by applying a hydrophilicity-imparting treatment (for example, application of a surface-active agent or heat embossing) to a part of a non-woven fabric constituting a breathable waterproof sheet; or may be formed by applying a hydrophilicity-imparting treatment on the entire non-woven fabric constituting a breathable waterproof sheet for providing liquid permeability to the entire sheet and then applying a hydrophobicity-imparting treatment (for example, application of wax) to a part of the sheet.

Patterns of the liquid-permeable portion may be formed (1) by forming strip-shaped liquid-permeable portions along both side edges of the skin-contact sheet, (2) by forming stripe-shaped liquid-permeable portions on the entire or a part of the skin-contact sheet, or (3) by forming dot-shaped liquid-permeable portions on the entire or a part of the skin-contact sheet. The patterns of the above (1) and (2) can be relatively readily formed by forming a liquid-permeable portion by applying a surface-active agent to a part of a non-woven fabric constituting a breathable waterproof sheet, or by applying a hydrophilicity-imparting treatment to the entire non-woven fabric constituting a breathable waterproof sheet for providing liquid permeability to the entire sheet and then bonding a breathable waterproof sheet to a part of this sheet for remaining the liquid-permeability in the remaining portion, for example. In addition, the pattern of the above (3) can be readily formed by forming a liquid-permeable portion by thermally embossing a part of a non-woven fabric constituting a breathable waterproof sheet.

It is preferable that the skin-contact sheet be partially composed of a liquid-permeable sheet and the liquid-permeable sheet serves as the liquid-permeable portion of the skin-contact sheet. For example, in the disposable diaper 1 shown in FIG. 3, a liner sheet 24*b*, which is a part of the skin-contact sheet 24, is composed of a liquid-permeable sheet 48, and the liquid-permeable sheet 48 serves as the liquid-permeable portion 50 of the skin-contact sheet 24.

Such a structure is preferable because of its flexibility of selection of constituent materials compared to that in a method for forming the liquid-permeable portion by applying a hydrophilicity-imparting treatment to a part of a non-woven fabric. More specifically, a constituent material of the liquid-permeable sheet may be a sheet composed of a liquid-permeable material (for example, a non-woven fabric applied with a hydrophilicity-imparting treatment) which may be used as a constituent material of a top sheet described below. In addition, a punched sheet (perforated sheet) prepared by punching a non-woven fabric or a liquid-permeable material (e.g., a resin film) or a mesh sheet may be used.

Additionally, it is preferable that the skin-contact sheet be composed of a laminate of a breathable waterproof sheet and a liquid-permeable sheet and that the laminate have a structure such that the breathable waterproof sheet is arranged at the central region of the liquid-permeable sheet and the liquid-permeable sheet protrudes from both sides of the breathable waterproof sheet.

When the skin-contact sheet is composed of a laminate of a breathable waterproof sheet and a liquid-permeable sheet, an opening-elastic member (described below) can be readily and certainly fixed by interposing the opening-elastic member between the breathable waterproof sheet and the liquid-permeable sheet. Furthermore, the breathable waterproof sheet is arranged at the central region of the skin-contact sheet where the skin of a wearer is readily brought into contact with, and the liquid-permeable sheets are arranged at the both side regions of the skin-contact sheet where the skin of a wearer is relatively negligibly brought into contact with. Therefore, urine on the skin-contact sheet can be introduced into the inside of the skin-contact sheet without a decrease in the effect of preventing urine backflow and feces backflow.

For example, in the disposable diaper 1 shown in FIG. 3, the skin-contact sheet 24 is composed of a laminate of an upper sheet 24*a* and a liner sheet 24*b*. The upper sheet 24*a* serves as the breathable waterproof sheet 46, and the liner sheet 24*b* serves as the liquid-permeable sheet 48. The breathable waterproof sheet 46 having a narrow width is arranged at the central region of the liquid-permeable sheet 48 having a broad width. Thus, the disposable diaper 1 has a structure such that the liquid-permeable sheet 48 protrudes from the both sides of the breathable waterproof sheet 46. The method for constituting the skin-contact sheet by combining these plurality of members is preferable because various functions and characteristics can be provided to the skin-contact sheet. That is, the skin-contact sheet can be provided with various functions and characteristics by optionally combining various types of members having a low liquid permeability (high water-pressure resistance), a low stimulation to skin, or a high cushion property, or containing functional agents.

As described above, when the skin-contact sheet is composed of a laminate of a breathable waterproof sheet and a liquid-permeable sheet, the positional relation between these sheets is not specifically limited. That is, the laminate may have a structure such that the liquid-permeable sheet is laminated on the top surface of the breathable waterproof sheet or that the breathable waterproof sheet is laminated on the top surface of the liquid-permeable sheet.

Preferably, the skin-contact sheet is composed of a laminate having a structure such that a breathable waterproof sheet is laminated on the top surface of a liquid-permeable sheet. Since the skin-contact sheet is a member which is provided in order to be brought into direct contact with skin, the feel is directly related to comfortableness of wearing. By constituting the skin-contact sheet as in above, the comfortableness of the skin-contact sheet can be maintained even if perspiration or urine is present on the skin-contact sheet. Thus, advantageously, comfortable wearing feeling can be achieved. For example, in the disposable diaper 1 shown in FIGS. 2 and 3, the laminate has a structure such that an upper sheet 24*a* composed of a breathable waterproof sheet 46 is laminated on the top surface of the liner sheet 24*b* composed of a liquid-permeable sheet 48.

It is necessary that the skin-contact sheet is provided with an opening (feces-passing opening) allowing passage of feces excreted by a wearer. With such a structure, feces excreted by a wearer pass through the skin-contact sheet and reach the top sheet. Thus, the opportunity that the feces are brought into direct contact with the skin of a wearer can be significantly decreased.

Shape of the opening is not specifically limited as long as the opening can allow passage of feces. That is, examples of the shape of the "opening" which allows passage of feces include openings (apertures) such as circular openings, elliptical openings, and rhombic openings; and slits such as linear slits, cross-shaped slit, and star-shaped slit formed by crossing three of more of slits. Among them, in particular, an elliptical opening having the major axis in the longitudinal direction (in the direction of the length) of a diaper and a star-shaped slit are preferable. The advantageousness in the elliptical opening is that feces can readily pass through the opening of the skin-contact sheet. The advantageousness in the star-shaped opening is that feces that have reached the top sheet through the opening of the skin-contact sheet can be sufficiently prevented from exuding through the opening of the skin-contact sheet again and thereby from soiling the buttocks of a wearer. In addition, the size of the aperture or slit may be optionally determined in consideration of the function of "allowing passage of feces".

The feces-passing opening preferably has a shape such that the opening area of the front half region (the front region) divided by a central line in the longitudinal direction of the feces-passing opening is larger than that of the rear half region (the rear region). More preferably, the feces-passing opening has a part where the width is the largest (the maximum opening portion) on the front region. Such a shape can efficiently prevent feces that have reached the top sheet by passing through the skin-contact sheet from adhering to the buttocks, in particular, the buttock gap of a wearer. On the other hand, since the opening area of the front region is large, it does not prevent feces from passing through.

For example, in the disposable diaper 1 shown in FIG. 2, the shape of the feces-passing opening 28a is approximately an anchor-like shape in such a manner that the front region has a part where the width extends toward the both side edges. That is, this part is the maximum opening portion, and therefore, in the disposable diaper 1, the feces-passing opening 28a has the opening area of the front region larger than that of the rear region and has the maximum opening portion in the front region. In this specification, the term "central line in the longitudinal direction" denotes a line which passes through the midpoint of a line extending in the longitudinal direction from the front end to the rear end of the feces-passing opening 28a and extends in the lateral direction of a diaper.

Furthermore, the skin-contact sheet may be provided with another opening for allowing passage of urine on the front part side with respect to the feces-passing opening. That is, the skin-contact sheet is preferably provided with a feces-passing opening and a urine-passing opening.

The urine-passing opening allows passage of urine excreted by a wearer and the urine can be certainly transferred into the inside of the skin-contact sheet. Therefore, diffusion of urine moving on the skin-contact sheet and side leakage from the opening around legs can be efficiently prevented. For example, in the disposable diaper 1 shown in FIG. 2, the skin-contact sheet 24 has the opening 28 consisting of an anchor-shaped feces-passing opening 28a and an elliptical urine-passing opening 28b. In this example, the feces-passing opening 28a is disposed on a part corresponding to the crotch portion 4, and the urine-passing opening 28b is disposed on a part of the front part 2 side with respect to the feces-passing opening 28a.

When the two openings (the feces-passing opening and the urine-passing opening) are provided as described above, an isolating wall is preferably provided in order to divide the space between the skin-contact sheet and the top sheet into a space connecting to the feces-passing opening and a space connecting to the urine-passing opening.

It has been reported that ammonia is generated by mixture of feces and urine, this ammonia alkalifies the circumstance, an enzyme in feces is highly activated in the alkaline atmosphere, and this activated enzyme and the generated ammonia cause inflammation on a weak area of skin and lead to diaper rash (K. Yamamoto, Hifu Rinsho (Clinical Dermatology) 30, pp. 949-956 (1998)). Since urine and feces excreted by a wearer can be absorbed and held in the diaper while maintaining the conditions that they are isolated from each other by providing the isolating wall described above, the urine and the feces are hardly mixed. Therefore, diaper rash can be effectively prevented.

Preferably, an elastic member (opening-elastic member) is arranged on the periphery of the opening. Since the elastic member applies a tension to the skin-contact sheet, the skin-contact sheet is provided with elasticity. Therefore, the skin-contact sheet can be prevented from falling in the top sheet side even if the skin-contact sheet is wasted. Consequently, the skin-contact sheet can be readily brought into contact with the skin of a wearer. In addition, by arranging the opening-elastic member, a force contracting the skin-contact sheet and bending the top sheet, the absorber, and the back sheet toward the lower side (wearing member side) can be generated. Therefore, the skin-contact sheet can be maintained so as to have a gap between the skin-contact sheet and the top sheet. Thus, the skin-contact sheet can be certainly apart from the top sheet.

The opening-elastic member can be suitably formed by using an elastic material used for known disposable diapers. Examples of such elastic material include rubber thread and flat rubber composed of an elastic material such as natural rubber or synthetic rubber (e.g., urethane rubber), elastic nets, elastic films, and elastic foams (e.g., urethane foam).

Pattern arrangement of the opening-elastic member is not specifically limited as long as the pattern can achieve the above-mentioned effects. Preferably, in order to certainly apply an elastic force to the opening, the pattern is arranged so that the opening-elastic member surrounds the periphery of the opening. For example, an opening-elastic member having a circular, elliptical, or rhombic pattern is arranged so as to surround the periphery of the opening.

An example of preferable embodiments of the opening-elastic member has a pattern arranged so that two opening-elastic members intersect each other at least one point at the front or rear side of the opening and surround a part of the periphery of the opening. By arranging the opening-elastic members in such a pattern, the opening-elastic members can be continuously arranged in the longitudinal direction of diapers. As a result, advantageously, sequential manufacturing of disposable diapers can be readily achieved.

For example, in the disposable diaper 1 shown in FIG. 2, the opening-elastic member 30 consists of two opening-elastic members 30a and 30b. The two opening-elastic members 30a and 30b intersect each other at a point P between the feces-passing opening 28a and the urine-passing opening 28b and are arranged so as to surround parts of the peripheries of the feces-passing opening 28a and the urine-passing opening 28b. By arranging the two opening-elastic members 30a and 30b in such a pattern, absorbent bodies arranged in a row, namely, the absorbent bodies 14 sequentially arranged in the longitudinal direction, can be readily manufactured.

In the disposable diaper 1 shown in FIG. 2, the opening-elastic members 30a and 30b are arranged so as to intersect each other at the center of the crotch portion 4. With such an arrangement, the elastic force in the width direction (the lateral direction of the diaper) at the crotch portion 4 (namely, near the point P) is higher than those at the front part 2 side or at the back part 6 side of the diaper. Therefore, the portion between the feces-passing opening 28a and the urine-passing opening 28b can be brought into contact with the skin of a wearer more tightly, though the portion is relatively readily loosened compared to other portions of the skin-contact sheet 24. In addition, in the disposable diaper 1 shown in FIG. 2, the opening-elastic members 30a and 30b do not intersect each other at points other than the point P on the center of the crotch portion 4. Consequently, the pattern is arranged so that a periphery on the back part 6 side of the feces-passing opening 28a and a periphery on the front part 2 side of the urine-passing opening 28b are opened. With such an arrangement, an excessively tight contact of the front part 2 side and the back part 6 side of the skin-contact sheet 24 with the skin of a wearer can be avoided. Consequently, air permeability can be obtained. Therefore, perspiration due to the abutting of the skin-contact sheet can be repressed, and stuffiness and skin irritation due to perspiration can be effectively prevented.

The opening-elastic member as described above is fixed to the skin-contact sheet by using an adhesive agent or other means. The fixing may be conducted, for example, by bonding using a hot-melt adhesive agent or other adhesive agents with high fluidity; by adhesion utilizing heat, such as heat-sealing; or by adhesion utilizing an ultrasonic wave.

The opening-elastic member is preferably fixed in the stretched state for applying sufficient elastic force to the opening. For example, when the opening-elastic member is composed of a natural rubber or a synthetic rubber, the opening-elastic member is preferably fixed in the stretched state of 100 to 400%, more preferably fixed in the stretched state of 200 to 300%. By fixing in the stretched state of such ranges, a sufficient elastic force can be applied to the opening, and the opening can be prevented from being contracted beyond necessity.

The arrangement of the opening-elastic member is not specifically limited. For example, as the disposable diaper 1 shown in FIG. 3, preferably, the skin-contact sheet 24 is constituted by bonding two sheet members (an upper sheet 24a and a liner sheet 24b) and is arranged so as to interpose the opening-elastic members 30a and 30b between the upper sheet 24a and the liner sheet 24b. By employing such an arrangement, an elastic force can be advantageously applied to the skin-contact sheet 24 by using a minimal amount of the elastic member.

Figure 7:
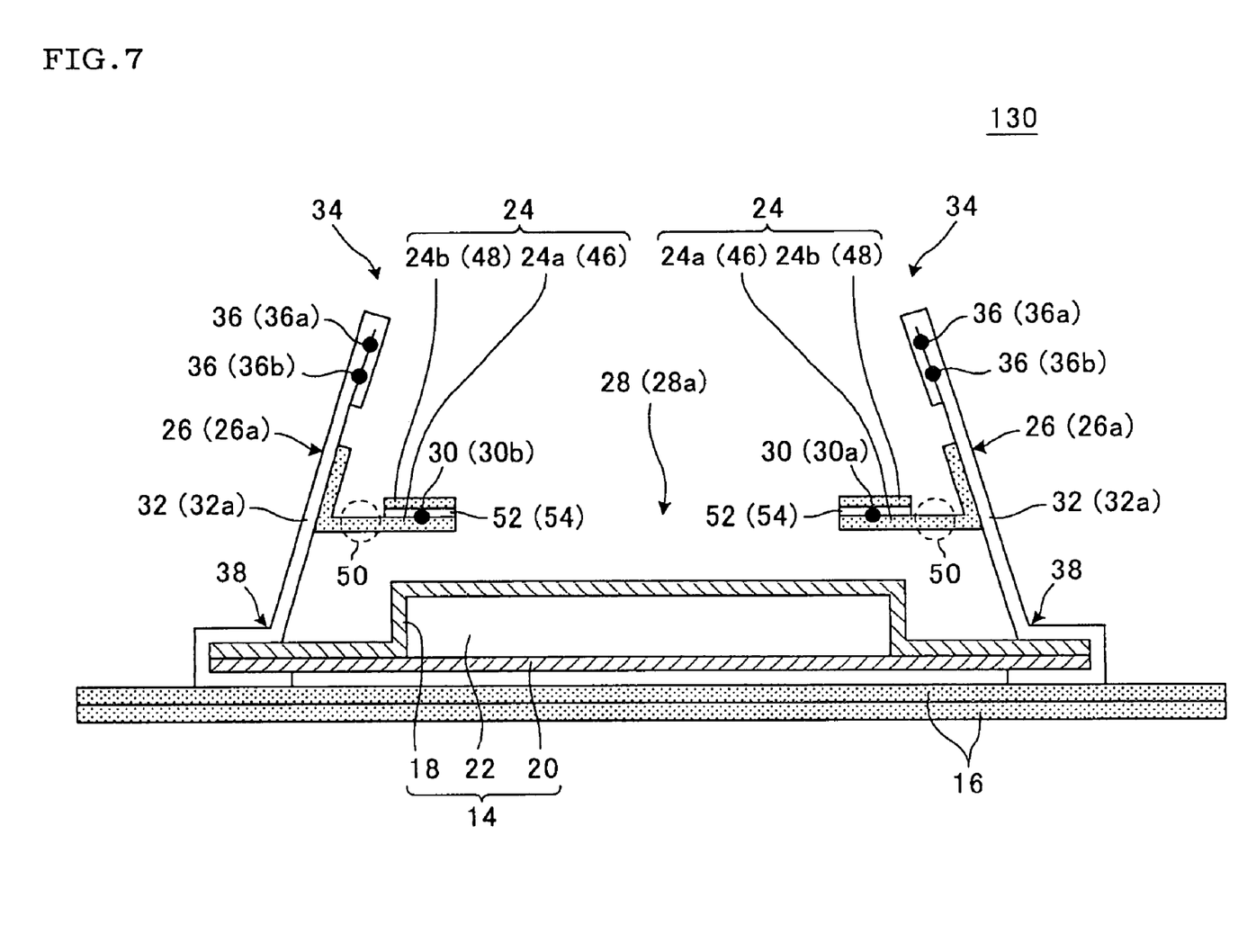
FIG. 7 is a schematic cross-sectional view of a disposable diaper according to another embodiment of the present invention, showing a cross section when the disposable diaper is cut at a crotch portion.
Figure 8:
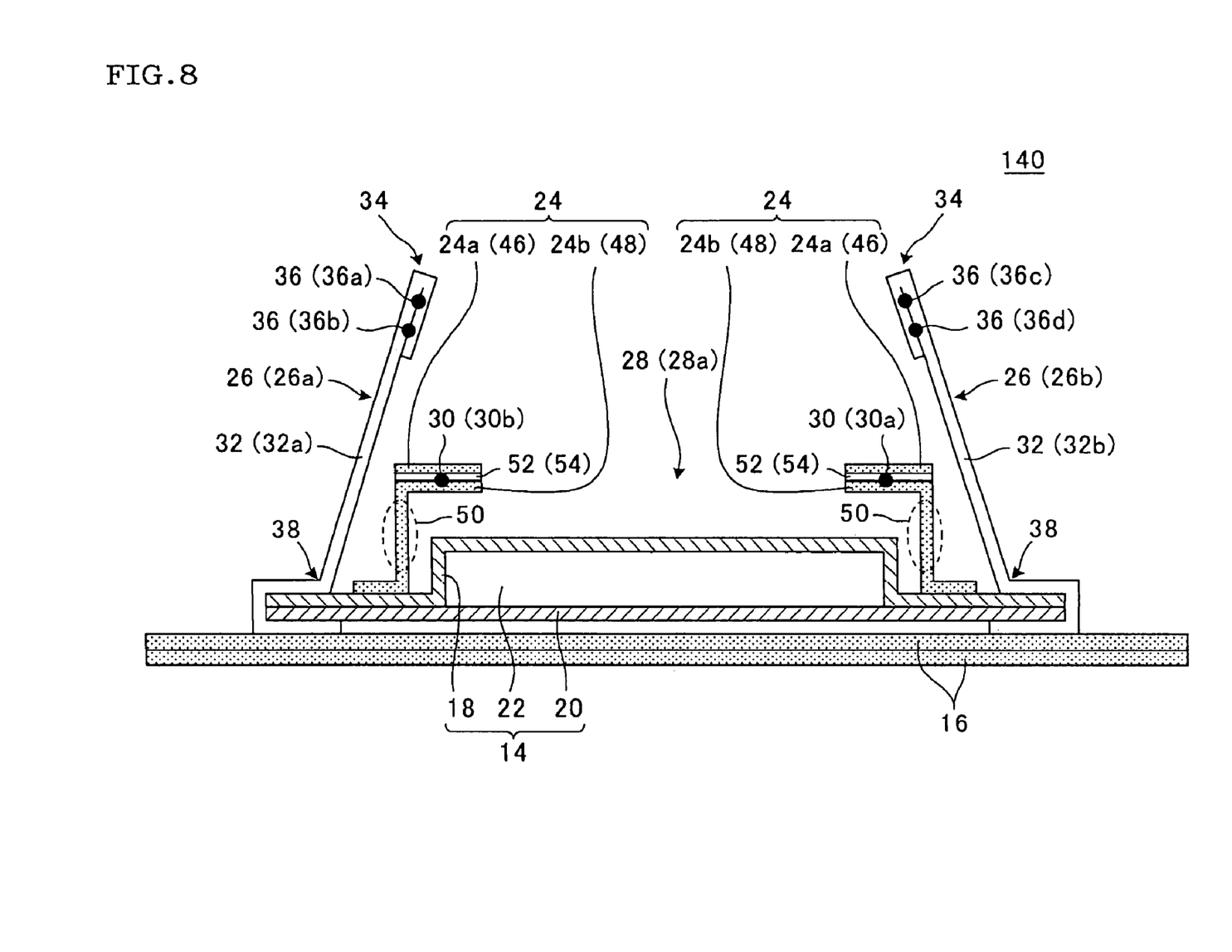
FIG. 8 is a schematic cross-sectional view of a disposable diaper according to another embodiment of the present invention, showing a cross section when the disposable diaper is cut at a crotch portion.

The skin-contact sheet may be fixed by (1) interposing the skin-contact sheet 24 in the bonding portions of sheet members 32a and 32b constituting standing gathers 26a and 26b, respectively, and the top sheet 18 (or the back sheet 20), as in the disposable diaper 1 shown in FIG. 3; or (2) fixing the skin-contact sheet 24 on the internal sides of the standing gathers 26a and 26b at portions between the upper edges 34 and the lower edges (standing lines 38) of the standing gathers 26a and 26b, as in the disposable diaper 130 shown in FIG. 7. In addition, the skin-contact sheet 24 may be fixed on the internal region surrounded by the pair of standing gathers without the contact with the standing gathers. For example, the skin-contact sheet may be fixed by (3) fixing the skin-contact sheet 24 on the absorbent body 14 at the bonding portion (so-called flap portion) of the top sheet 18 and the back sheet 20 within the region surrounded by the standing gathers 26a and 26b, as in the disposable diaper 140 shown in FIG. 8. Among these methods, the method (1) is preferable from the viewpoint that the effect for bringing the skin-contact sheet into contact with skin of a wearer is high.

(1-2) Standing Gathers:

The standing gathers is a member for preventing side leakage of urine excreted by a wearer and is constituted so as to serve as three-dimensional leakage-preventing walls by rising. The disposable diaper according to the present invention is preferably provided with at least a pair of standing gathers on the respective sides of the skin-contact sheet. These standing gathers serve as leakage-preventing walls and urine leakage from the openings around legs of a diaper (so-called "side leakage") can be efficiently prevented even if urine excreted on the skin-contact sheet is diffused by moving on the skin-contact sheet. Incidentally, the word "standing gather(s)" may be expressed as "barrier cuff".

Structures of standing gathers used in known disposable diapers and other absorbent products may be employed as the structure of the standing gathers of the diaper according to the present invention. For example, the standing gathers may be suitably formed by arranging an elastic member (standing gathering elastic member) on a part of a sheet member and thereby forming gathers (wrinkles) on the sheet member with the standing gathering elastic member.

It is preferable that the sheet member constituting the standing gathers is a water-repellent material from the viewpoint of improving the leakage-preventing property of the standing gathers. Materials having water repellency may be the same materials as those used as the breathable waterproof sheet described in the paragraph of the skin-contact sheet.

The standing gathers may be formed by folding the top sheet or the back sheet of the absorber body, but it is preferable that the standing gathers are formed by bonding a sheet member which is made of a material completely different from those for the top sheet or the back sheet. For example, in the disposable diaper 1 shown in FIGS. 2 and 3, a pair of standing gathers 26a and 26b is formed by bonding sheet members 32a and 32b composed of a material completely different from those of the top sheet 18 or the back sheet 20 on the respective side edges of the absorbent body 14.

The standing gathering elastic member may be formed by using the same elastic material as that used in the opening-elastic member described above. In addition, a single standing gathering elastic member may be provided to one standing gathers, or a plurality of standing gathering elastic members may be provided to one standing gathers. The arranging position of the standing gathering elastic member is not specifically limited. For example, the standing gathering elastic member may be arranged near the lower edge (standing line) of the standing gathers or may be arranged between the upper edge and the lower edge (standing line) of the standing gathers. Preferably, a single or a plurality of opening-elastic members is arranged near the upper edge of the standing gathers in order to improve the rising property of the standing gathers.

For example, in the disposable diaper 1 shown in FIGS. 2 and 3, the standing gathering elastic members 36 are arranged near the upper edges 34 of the standing gathers 26a and 26b. The sheet members 32a and 32b are folded at the ends (the ends on the sides corresponding to the upper edges 34 of the standing gathers 26a and 26b), and two standing gathering elastic members 36a and 36b and two standing gathering elastic members 36c and 36d are arranged so as to be sandwiched by the folded portions of the sheet members 32a and 32b, respectively.

The height (the length from the lower edge to the upper edge) of the standing gathers is preferably 5 to 80 mm, more preferably 10 to 40 mm. By providing standing gathers having a height of 5 mm or more, leakage prevention can be sufficiently achieved. Furthermore, by providing standing gathers having a height of 80 mm or less, disadvantageousness such that the standing gathers cover the surfaces of the skin-contact sheet and the top sheet and thereby the absorbing properties of the sheets are inhibited can be avoided.

The standing gathers may be (1) an inward-folding gathers that the standing gathers are bent toward the inside of a diaper, (2) an outward-folding gathers that the standing gathers are bent toward the outside of a diaper, and (3) standing gathers partially provided with a bending portion or a folding portion (C-shaped folding gathers or Z-shaped folding gathers) in the height direction. Among these gathers, the inward-folding gathers are preferable because of their high leakage-preventing property. For example, the disposable diaper 1 shown in FIGS. 2 and 3 is provided with inward-folding type standing gathers 26a and 26b.

The standing gathers are preferably disposed on both sides of the skin-contact sheet from the viewpoint of preventing the side leakage of urine. In particular, it is preferable that the standing gathers are disposed along both side edges of the skin-contact sheet. With such a constitution, side leakage from the openings around legs can be efficiently prevented by the standing gathers certainly serving as leakage-preventing walls even if urine excreted on the skin-contact sheet is diffused by moving on the skin-contact sheet.

For example, in the disposable diaper 1 shown in FIGS. 2 and 3, the skin-contact sheet 24 is arranged so as to reach both side edges of the absorbent body 14, and the standing gathers 26a and 26b are disposed along both side edges of the skin-contact sheet 24, namely, along both side edges of the absorbent body 14. The disposable diaper 1 shown in FIGS. 2 and 3 is an example such that the standing gathers 26a and 26b are disposed along the entire side edges of the absorbent body 14, but the standing gathers 26a and 26b may be arranged at least on a portion corresponding to the crotch portion from the viewpoint of preventing the side leakage of urine.

The standing gathers are preferably disposed so that the upper edge of the gathers are arranged at a position upper than that of the surface of the skin-contact sheet. With such a constitution, leakage of urine to the outside by climbing out the standing gathers can be prevented even if urine excreted on the skin-contact sheet is diffused by moving on the skin-contact sheet.

In order to arrange the standing gathers so that the upper edge of the gathers are arranged at a position upper than that of the surface of the skin-contact sheet, the lower edges of the standing gathers may be arranged on the surface of the skin-contact sheet. That is, in the disposable diaper according to the present invention, the lower edges of the standing gathers are preferably arranged on the surface of the skin-contact sheet. With such a constitution, the upper edges of the standing gathers are certainly arranged at a position upper than the surface of the skin-contact sheet. Leakage of urine to the outside by climbing out the standing gathers can be certainly prevented by properly adjusting the height of the standing gathers according to the height of the surface of the skin-contact sheet.

For example, in the disposable diaper 1 shown in FIG. 3, the skin-contact sheet 24 is fixed so as to be interposed in the bonding part of the standing gathers 26a and 26b and the top sheet 18. Consequently, the lower edges of the standing gathers 26a and 26b are arranged on the surface of the skin-contact sheet 24, and the upper edges 34 of the standing gathers 26a and 26b are arranged at positions upper than that of the surface of the skin-contact sheet 24. In this specification, the term "lower edges of the standing gathers" refers to, as shown in FIG. 3, the fixing ends of the standing gathers 26a and 26b, namely, the parts of the standing lines 38.

The disposable diaper according to the present invention is preferably provided with at least a pair of standing gathers. However, two pairs or more of standing gathers may be provided.

(1-3) Absorber:

The absorber serves as a member for absorbing and holding urine excreted by a wearer. The absorber is composed of an absorptive material in order to absorb and hold urine and body fluids of a wearer.

Examples of the absorptive material constituting the absorber include known absorptive materials generally used in disposable diapers and other absorbent products, such as fluff pulp, a super-absorbent polymer (hereinafter referred to as "SAP"), and a hydrophilic sheet. Preferably, the fluff pulp may be wood pulp or non-wood pulp fibrillated into a cotton-like material; the SAP may be sodium polyacrylate; and the hydrophilic sheet may be a tissue, an absorbing paper, or a non-woven fabric provided with hydrophilicity.

These absorptive materials are generally used as a single-layered or multilayered mat. These mats may be composed of one kind of the above-mentioned absorptive materials or a combination of at least two kinds thereof. Among them, a combination of 100 parts by weight of fluff pulp and about 10 to 500 parts by weight of SAP is preferable. In such a combination, SAP may be uniformly mixed in each mat of fluff pulp, or a layer of SAP may be arranged between layers of the multilayered fluff pulp.

The absorber may be preferably interposed between at least a part of the top sheet and the back sheet. In general, the absorber is arranged between the top sheet and the back sheet by interposing the absorber between the top sheet and back sheet and sealing the peripheries thereof. Therefore, a flap where the absorber is not interposed between the top sheet and the back sheet is formed on the periphery of the absorber.

Preferably, the entire absorber is enveloped by a hydrophilic sheet. In such a constitution, advantageously, leakage of SAP from the absorber can be prevented and shape stability of the absorber can be achieved.

The shape of the absorber is not specifically limited, and shapes of known disposable diapers and other absorbent products, such as a rectangular, hourglass-shaped, gourd-shaped, or T-shaped absorber, may be employed.

(1-4) Top Sheet:

The top sheet is arranged so as to cover the top surface, i.e., the surface located at the side facing the skin of a wearer when a diaper is worn by the wearer, of the absorber. At least a part of the top sheet, namely, the entire top sheet or a part of the top sheet, is composed of a liquid-permeable material for allowing urine of a wearer to be absorbed by the absorber arranged below the top sheet.

Examples of the liquid-permeable material constituting the top sheet include woven fabrics, non-woven fabrics, and porous films. Among them, a hydrophilicity-imparted non-woven fabric composed of a thermoplastic resin such as polypropylene, polyethylene, polyester, or nylon is preferably used.

The top sheet may be composed of a single sheet member or a plurality of sheet members. For example, in a tape-type diaper described below, a top sheet (central sheet) composed of a liquid-permeable material is arranged on the central part of the diaper. Another top sheet (side sheet) composed of a breathable waterproof material is arranged at the flap part of the diaper. The breathable waterproof material is resistive to the permeation of liquid.

(1-5) Back Sheet:

The back sheet is arranged so as to cover the bottom surface, i.e., the surface located at the side facing the clothing of a wearer when a diaper is worn by the wearer, of the absorber.

The back sheet is composed of a liquid-impermeable material for preventing leakage of urine of a wearer to the outside of the diaper.

Examples of the liquid-impermeable material constituting the back sheet include liquid-impermeable films composed of resins such as polyethylene. In particular, a microporous polyethylene film is preferable. This microporous polyethylene film is provided with a large number of fine pores having a diameter of one tenth to several micrometers. Therefore, the film is liquid impermeable, but is moisture permeable. Consequently, stuffiness in the inside of a diaper can be advantageously prevented.

In addition, a sheet member (covering sheet) may be bonded on the outer surface of the back sheet. This covering sheet reinforces the back sheet and improves the touch (feel) of the back sheet.

Examples of a material constituting the covering sheet includes woven fabrics and non-woven fabrics. In particular, a dry non-woven fabric and a wet non-woven fabric composed of a thermoplastic resin such as polyethylene, polypropylene, or polyester is preferable.

(1-6) Absorbent Body:

In a pants-type diaper composed of two pieces, a top sheet, a back sheet, and an absorber are constituted as one member, i.e., an "absorbent body", responsible for absorbing and holding functions. A disposable diaper is constituted by bonding the absorbent body to a separately manufactured wearing member. The absorbent body has a structure such that the top sheet is arranged at the upper side of the absorber and the back sheet is arranged at the lower side of the absorber and thereby the absorber is interposed between the top sheet and the back sheet. For example, in the disposable diaper 1 shown in FIG. 3, an absorbent body 14 having a structure composed of an absorber 22 interposed between a top sheet 18 and a back sheet 20 is formed by interposing the absorber 22 between the top sheet 18 and the back sheet 20 and sealing the periphery of the absorber 22.

The absorbent body has a size at least covering a crotch portion of a diaper. Preferably, the absorbent body has a size covering not only the crotch portion but also parts of a front part and a back part in order to certainly prevent leakage. The absorbent body may be fixed to a wearing member by using an adhesive agent such as a hot-melt adhesive agent.

(1-7) Wearing Member:

The wearing member is responsible for attaching the diaper so as to wrap the body of a wearer. Specifically, the wearing member is a sheet-like member for providing a front part, a crotch portion, and a back part.

In a pants-type diaper composed of two pieces, functions for absorbing and holding excrements of a wearer are exclusively performed by the absorbent body. The wearing member is not necessarily composed of a liquid-impermeable material. Examples of the material constituting the wearing member include non-woven fabrics composed of a synthetic fiber of polyethylene, polypropylene, polyester, or other thermoplastic resins.

The wearing member is generally constituted by bonding two or more pieces of non-woven fabrics so as to sandwich and fix leg elastic members. For example, in the disposable diaper 1 shown in FIGS. 1 to 3, the wearing member 16 is composed of two pieces of non-woven fabrics; and a leg elastic member 40, a waist elastic member 42, and an abdomen elastic member 44 are interposed and fixed between these two pieces of non-woven fabrics.

(1-8) Elastic Members:

In a pants-type disposable diaper, in general, a leg elastic member and a waist elastic member are arranged. Preferably, an abdomen elastic member is further arranged.

The leg elastic member is arranged along the openings around legs. By arranging this leg elastic member, gathers (leg gathers) abounding in the elastic property can be provided to the opening around legs. Therefore, gaps around the legs of a wearer are hardly formed and urine-leakage from the openings around legs can be effectively prevented.

The waist elastic member is arranged along the opening around waist. By arranging this waist elastic member, gathers (waist gathers) abounding in the elastic property can be provided to the opening around waist. Therefore, gaps around the waist of a wearer are hardly formed and urine-leakage from the opening around waist can be prevented. In addition, the diaper can favorably fit a wearer and is prevented from slipping down.

The abdomen elastic member is arranged at a portion between the opening around waist and the opening around legs (i.e., portion corresponding to the abdomen of a wearer). By arranging this abdomen elastic member, tummy gathers abounding in the elastic property can be provided to the portion corresponding to the abdomen of a wearer. With a combination of this tummy gathers and the waist gathers, the diaper can further favorably fit a wearer and is further prevented from slipping down.

In the disposable diaper 1 shown in FIGS. 1 and 2, a plurality of leg elastic members 40 are arranged on the periphery of the openings around legs 12*a* and 12*b*; a plurality of waist elastic members 42 are arranged on the periphery of the opening around waist 10 so as to surround the opening around waist 10; and a plurality of abdomen elastic members 44 are arranged on a portion between the opening around waist 10 and the openings around legs 12*a* and 12*b* (i.e., portion corresponding to the abdomen of a wearer) so as to surround the abdomen of a wearer.

These elastic members may employ the same constitute as that of the above-mentioned elastic members for the openings. The constituting material, an elongation ratio of the material, and an elongated state of the material when fixed may be determined depending on a degree of the elasticity of gathers.

(2) Manufacturing Method:

A method for manufacturing the disposable diaper 1 (a pants-type diaper composed of two pieces) shown in FIGS. 1 to 3 will now be described as an example of a method for manufacturing a disposable diaper according to the present invention.

(2-1) Manufacturing of Absorbent Body:

An absorber 22 wrapped with a hydrophilic sheet is arranged on the top surface of a back sheet 20, and a top sheet 18 is further arranged on the absorber 22. Then, the top sheet 18 and the back sheet 20 are sealed so as to sandwich the periphery of the absorber 22 to obtain a absorbent body 14.

(2-2) Manufacturing of Skin-Contact Sheet:

Two opening-elastic members 30*a* and 30*b* are arranged on the top surface of a liner sheet 24*b* with a predetermined pattern, and the liner sheet 24*b* is bonded to an upper sheet 24*a*. The size of this upper sheet 24*a* is determined so that the upper sheet 24*a* covers only the central region of the liner sheet 24*b* and that the both side regions of the liner sheet 24*b* are exposed. A hot-melt adhesive agent is used for bonding the liner sheet 24*b* and the upper sheet 24*a*, and a hot-melt adhesive layer 54 such that the coated amount of the agent is in the range of 15 to 40 g/m² is formed. This hot-melt adhesive layer 54 serves as the liquid-permeation resistive layer 52.

The two opening-elastic members 30a and 30b intersect each other at a point P between a feces-passing opening 28a and a urine-passing opening 28b which are formed afterward. The opening-elastic members 30a and 30b are arranged with a pattern partially surrounding the peripheries of the feces-passing opening 28a and the urine-passing opening 28b.

Then, the bonded liner sheet 24b and the upper sheet 24a are provided with a feces-passing opening 28a and a urine-passing opening 28b. Thus, a skin-contact sheet 24 is obtained. The skin-contact sheet 24 has a two-layer structure and is provided with two opening-elastic members 30a and 30b intersecting each other at the point P between the feces-passing opening 28a and the urine-passing opening 28b and being arranged with a pattern partially surrounding the feces-passing opening 28a and the urine-passing opening 28b.

(2-3) Manufacturing of Standing Gathers:

One end of a sheet member 32a (32b) is folded, and two standing gathering elastic members 36a and 36b (36c and 36d) are interposed to the folded part. The folded part having the elastic members 36a and 36b (36c and 36d) is bonded to obtain standing gathers 26a (26b).

(2-4) Attachment of Skin-Contact Sheet and Other Parts to Absorbent Body:

A skin-contact sheet 24 (liner sheet 24b) is bonded to the surface of the top sheet 18 constituting the absorbent body 14, and then the standing gathers 26a and 26b are bonded so as to sandwich the side edges of the absorbent body 14 and the skin-contact sheet 24 (liner sheet 24b).

(2-5) Manufacturing of Wearing Member:

A waist elastic member 42, an abdomen elastic member 44, and a leg elastic member 40 are arranged and adhesively fixed on the top surface of one piece of non-woven fabric, and another one piece of non-woven fabric is further laminated and fixed. Thus, a wearing member 16 having the waist elastic member 42, the abdomen elastic member 44, and the leg elastic member 40 between the two pieces of the non-woven fabrics is prepared.

(2-6) Manufacturing of Disposable Diaper:

The absorbent body 14 is arranged and fixed near the crotch portion of the wearing member 16. Then, the resulting wearing member 16 is folded into two by adjusting the front part 2 and the back part 6 so that the absorbent body 14 is on the inside. The front part 2 and the back part 6 are joined by heat-sealing so as to form a joining part 8. Thus, the disposable diaper 1 shown in FIGS. 1 to 3 can be manufactured.

(3) Application of the Present Invention:

The disposable diaper according to the present invention can be applied to not only a pants-type diaper composed of two pieces but also, for example, a pants-type diaper composed of one piece and a tape-type diaper. That is, the effects of the disposable diaper according to the present invention can be accomplished in these disposable diapers by arranging the skin-contact sheet at a position upper than that of the surface of the top sheet and providing at least a pair of standing gathers.

The "one piece-type" diaper is provided with a top sheet, a back sheet, and an absorber like the two-piece-type diaper, but the absorber responsible for the absorbing and holding functions is interposed (enclosed) between the top sheet and the back sheet and is integrally structured with the top sheet and/or the back sheet which are responsible for wearing functions.

The "tape-type diaper" is provided with a top sheet, a back sheet, an absorber interposed between at least a part of the top sheet and the back sheet, and a tape fastener for wearing. In the tape-type diaper, the front part and the back part of the diaper can be fixed to each other with the tape fastener. In the "tape-type diaper", there are a "one-piece-type" diaper and a "two-piece-type" diaper as in the pants-type diaper. The disposable diaper according to the present invention can be applied to both types in the tape-type diaper.

The disposable diaper according to the present invention can be suitably used as diapers for infants or elderly or disabled persons who require nursing care. In the disposable diaper according to the present invention, the skin of a wearer is negligibly brought into direct contact with excreted feces, and the urine backflow and feces backflow are low. Therefore, the disposable diapers according to the present invention can be suitably used as disposable diapers, in particular, for infants, whose skin are weak and, therefore, have many troubles.

What is claimed is:

1. A disposable diaper comprising:
    an absorber;
    a top sheet at least partially comprising a liquid-permeable material and arranged to cover a top surface of the absorber;
    a back sheet comprising a liquid-impermeable material and arranged to cover a bottom surface of the absorber; and
    a skin-contact sheet arranged over the top sheet and having a feces-passing opening formed therein, the skin-contact sheet at least partially comprising a laminated structure defined by a breathable waterproof sheet layer comprising a non-woven fabric, a liquid-permeation resistive layer and a liquid permeable sheet layer comprising a non-woven fabric having a hydrophilicity-imparting agent applied thereto, arranged in that order.

2. The disposable diaper according to claim 1, wherein the liquid-permeation resistive layer comprises a hot-melt adhesive layer composed of a coated hot-melt adhesive in the range of 15 to 40 g/m², and the hot-melt adhesive layer is disposed on the lower side of the breathable waterproof sheet layer of the skin contact sheet.

3. The disposable diaper according to claim 2, wherein a water-repellent agent layer including a water-repellent agent containing a wax is provided on an upper side of the breathable waterproof sheet layer of the skin contact sheet.

4. The disposable diaper according to claim 1, wherein the breathable waterproof sheet layer is arranged at a central region of the liquid-permeable sheet layer and the liquid-permeable sheet layer protrudes from both sides of the breathable waterproof sheet layer.

5. The disposable diaper according to claim 4, further comprising:
    at least a pair of standing gathers disposed on the respective side edges of the skin-contact sheet and adapted to rise and serve as leakage-preventing walls.

6. The disposable diaper according to claim 1, further comprising:
    at least a pair of standing gathers disposed on the respective side edges of the skin-contact sheet and adapted to rise and serve as leakage-preventing walls.

7. The disposable diaper according to claim 1, wherein a water-repellent agent layer including a water-repellent agent containing a wax is provided on an upper side of the breathable waterproof sheet layer of the skin contact sheet.

* * * * *